(12) United States Patent
Street et al.

(10) Patent No.: US 6,589,188 B1
(45) Date of Patent: Jul. 8, 2003

(54) METHOD FOR MONITORING HEART FAILURE VIA RESPIRATORY PATTERNS

(75) Inventors: Anne M. Street, Sunnyvale, CA (US); Matthew G. Fishler, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/566,295

(22) Filed: May 5, 2000

(51) Int. Cl.[7] .................................................. A61B 5/00
(52) U.S. Cl. ........................ 600/538; 600/529; 600/508; 607/17
(58) Field of Search ................................. 600/508–509, 600/513, 547, 538, 529, 533, 534; 607/4, 5, 9, 17–18, 20, 23, 24

(56) References Cited

U.S. PATENT DOCUMENTS

| | | | |
|---|---|---|---|
| 4,716,887 A | 1/1988 | Koning et al. | 128/419 PG |
| 5,020,541 A | 6/1991 | Marriott | 128/723 |
| 5,207,219 A | 5/1993 | Adams et al. | 128/419 |
| 5,271,395 A | 12/1993 | Wahlstrand et al. | 607/9 |
| 5,300,093 A | 4/1994 | Koestner et al. | 607/32 |
| 5,438,983 A | 8/1995 | Falcone | 128/630 |
| 5,441,523 A | 8/1995 | Nappholz | 607/14 |
| 5,562,712 A | 10/1996 | Steinhaus et al. | 607/20 |
| 5,605,151 A | 2/1997 | Lynn | 128/633 |
| 5,713,937 A | 2/1998 | Nappholz et al. | 607/30 |
| 5,738,102 A | 4/1998 | Lemelson | 128/671 |
| 5,792,197 A | 8/1998 | Nappholz | 607/17 |
| 5,824,020 A | 10/1998 | Cooper | 607/17 |
| 5,862,803 A | 1/1999 | Besson et al. | 128/696 |
| 5,876,353 A | 3/1999 | Riff | 600/547 |
| 5,935,081 A * | 8/1999 | Kadhiresan | 600/513 |
| 5,957,861 A | 9/1999 | Combs et al. | 600/547 |
| 6,104,949 A | 8/2000 | Pitts Crick et al. | 600/547 |
| 6,135,966 A | 10/2000 | Ko | 600/481 |
| 6,264,606 B1 | 7/2001 | Ekwall et al. | 600/300 |
| 6,264,611 B1 | 7/2001 | Ishikawa et al. | 600/486 |
| 6,275,727 B1 * | 8/2001 | Hopper et al. | 600/513 |
| 6,336,903 B1 | 1/2002 | Bardy | 600/508 |
| 6,409,675 B1 * | 6/2002 | Turcott | 600/508 |
| 6,454,719 B1 | 9/2002 | Greenhut | 600/484 |
| 6,459,929 B1 | 10/2002 | Hopper et al. | 600/513 |

FOREIGN PATENT DOCUMENTS

| | | | |
|---|---|---|---|
| DE | 25 27 475 A1 | 12/1976 | A61B/5/00 |
| FR | 2 664 487 A1 | 1/1992 | A61B/5/08 |
| WO | WO 86/07248 | 5/1986 | A61B/5/02 |

OTHER PUBLICATIONS

U.S. patent application Ser. No. 09/566,193, Turcott, filed May 5, 2000.

* cited by examiner

*Primary Examiner*—Robert L. Nasser
(74) *Attorney, Agent, or Firm*—Steven M. Mitchell

(57) ABSTRACT

Detection and monitoring of periodic breathing (PB) to provide an indication of changes in the hemodynamic status of a heart failure patient is accomplished by monitoring at least one of four independent physiologic parameters. The physiologic parameters are respiratory tidal volume, respiratory rate (B-B interval), arterial oxygen saturation ($SaO_2$) and heart rate (R-R interval). The data collected of these physiologic measures may then be analyzed by performing power spectral analysis or thresholding/binning. Each analysis method can be applied to each measure or combination thereof. In the preferred embodiment, the physiologic measures are made when the patient has been identified as being at rest or asleep to prevent interference from activity-related respiratory variations.

22 Claims, 4 Drawing Sheets

METHOD FOR MONITORING HEART FAILURE VIA RESPIRATORY PATTERNS

BACKGROUND OF THE INVENTION

I. Field of the Invention

This invention relates generally to implantable monitoring devices and implantable cardiac therapy devices, and more particularly to a method for monitoring the respiratory patterns of a chronic heart failure patient to track changes in disease state.

II. Description of the Related Art

Congestive heart failure (CHF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

CHF has been classified by the New York Heart Association (NYHA). Their classification of CHF corresponds to four stages of progressively worsening symptoms and exercise capacity from Class I to Class IV. Class I corresponds to no limitation wherein ordinary physical activity does not cause undue fatigue, shortness of breath, or palpitation. Class II corresponds to slight limitation of physical activity wherein such patients are comfortable at rest, but where ordinary physical activity results in fatigue, shortness of breath, palpitations, or angina. Class III corresponds to a marked limitation of physical activity wherein, although patients are comfortable at rest, less than ordinary activity will lead to symptoms. Lastly, Class IV corresponds to inability to carry on any physical activity without discomfort, wherein symptoms of CHF are present even at rest and where with any physical activity, increased discomfort is experienced.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in 1 out of 200 cases, heart transplantation is also available. Other cardiac surgery is also indicated for only a small percentage of patients with particular etiologies. Although advances in pharmacological therapy have significantly improved the survival rate and quality of life of patients, patients in NYHA Classes III or IV, who are still refractory to drug therapy, have a poor prognosis and limited exercise tolerance. Cardiac pacing has been proposed as a new primary treatment for patients with drug-refractory CHF.

Heart failure patients require close medical management to reduce morbidity and mortality. Because the disease status evolves with time, frequent physician follow-up examinations are often necessary. At follow-up, the physician may make adjustments to the drug regimen in order to optimize therapy. This conventional approach of periodic follow-up may be less satisfactory for heart failure, in which acute, life-threatening exacerbations can develop between physician follow-up examinations. It is well known among clinicians that if a developing exacerbation is recognized early, it can be more easily and inexpensively terminated, typically with a modest increase in oral diuretic. However, if it develops beyond the initial phase, an acute heart failure exacerbation becomes difficult to control and terminate. Hospitalization in an intensive care unit is often required. It is during an acute exacerbation of heart failure that many patients succumb to the disease. Early identification may also allow for pacing therapy from an implanted pulse generator.

In patients with CHF, alterations of breathing patterns such as Cheyne-Stokes respiration or periodic breathing have been identified during both day- and night-time. Periodic breathing is defined as a waxing and waning of tidal volume without periodic phases of apnea, whereas Cheyne-Stokes respiration is defined as a type of periodic breathing that includes periods of apnea between the phases of hyperventilation (hyperpnea) and hypoventilation (hypopnea.) These alterations of breathing are associated with marked oscillations of arterial oxygen saturation and heart rate.

Detection of periodicity and the underlying frequency content of a signal such as arterial oxygen saturation, breath to breath interval, tidal volume amplitude or heart rate (R to R intervals) can be accomplished via any of several widely used techniques of power spectral analysis. These techniques include, but are not limited to, periodogram estimation, the maximum entropy (all poles) method and the Blackman-Tukey algorithm.

Conventional cardiac monitors, such as defibrillators, pacemakers, Holter monitors, and cardiac event records, are tailored for the diagnosis and/or therapy of abnormalities of the cardiac electrical system. In contrast, heart failure is a disease of the cardiac mechanical system: it is primarily a failure of the myocardium to meet the mechanical pumping demands required of it. In monitoring the status of a heart failure patient, measuring the mechanical hemodynamic variables is clearly desirable. Examples of mechanical hemodynamic variables include atrial, ventricular, and arterial pressures, and cardiac output (volume of blood pumped into the aorta per unit time). However, because of the complex feedback network that monitors and controls cardiac performance, measuring variables that do not directly reflect the mechanical performance of the heart is also useful.

Some limitations of monitoring systems have been addressed by the development of an implantable system that monitors hemodynamic status (Medtronic Chronicle, Medtronic, Inc., Minneapolis, Minn.). While this system potentially avoids the need for active patient participation in disease state monitoring, it relies on an intravascular pressure transducer placed in the right ventricle of the heart. Examples of other hemodynamic monitoring systems include U.S. Pat. No. 5,454,838 in which Vallana et al. teach placement of a sensor on the myocardial wall using an intravascular approach. In U.S. Pat. No. 5,496,351, Plicchi et al. propose placing a sensor within the myocardial wall. Mortazavi in U.S. Pat. No. 5,040,538 and Cohen et al. in U.S. Pat. No. 4,815,469 describe placement of an optical sensor within the right ventricle.

An Implantable Ambulatory Electrocardiogram Monitor is described by Nappholz et al. in U.S. Pat. No. 5,113,869, incorporated herein by reference. This device is designed for chronic extravascular implantation. In contrast to cardiac recorders, it performs analysis on the electrocardiogram signal in order to predict imminent cardiac arrhythmias and to detect cardiac ischemia. Like the cardiac recorders, it is capable of storing raw ECG data for later review by a physician. This feature, along with the record of arrhythmic events it detected, allows the physician to tailor pharmacologic therapy. In addition, Nappholz et al. mention the use of transthoracic impedance for minute ventilation, ultrasound transducers for arterial pressure, or other sensors to allow discrimination of arrhythmias from normal cardiac rhythms caused by exertion or physiologic stress.

The use of impedance plethysmography, also called minute ventilation or minute volume, to control an exercise responsive or rate adaptive pacemaker is well know in the art. See for example U.S. Pat. No. 4,702,253 to Nappholz et al., U.S. Pat. No. 5,197,467 to Steinhaus et al. and U.S. Pat. No. 5,562,711 to Yerich et al., which patents are incorporated herein by reference. Minute ventilation is defined by the equation:

$$V_E = RR \times TV$$

where RR=respiration rate in breaths per minute, and TV=tidal volume in liters.

Clinically, the measurement of $V_E$ is performed by having the patient breathe directly into a device that measures the exchange of air and computing the total volume per minute. The direct measurement of $V_E$ is not practical with an implanted device. However, measurement of the impedance changes of the thoracic cavity can be implemented with an implanted pacemaker, and transthoracic impedance has been shown to correlate well with $V_E$. A pacemaker that is provided with impedance measurement capabilities is disclosed in the Nappholz et al. '253 patent mentioned above. The magnitude of the change of the impedance signal corresponds to the tidal volume and the frequency of change corresponds to respiration rate. Thus, measurement of thoracic impedance can be used as one method for obtaining both respiratory rate and tidal volume data.

In practice, thoracic impedance can be measured through assessment of the impedance present between two or more cardiac electrodes, such as the electrodes otherwise used for pacing and/or sensing in connection with a cardiac pacemaker. In particular, it has been shown that thoracic impedance can be measured by delivering constant-current excitation pulses between two "source" electrodes, such that the current is conducted through some region of the thoracic cavity. The voltage differential between two "recording" electrodes can then be measured to ascertain the impedance as reflected by the voltage differential arising from the conduction of the excitation current pulses through the thorax.

Because of the considerations described above, the principal object of the present invention is to provide a method for use of a device that monitors a patient's hemodynamic status.

Another object of the invention is to monitor the status of a patient with chronic heart failure in order to optimize patient therapy.

A further object is to monitor the status of a chronic heart failure patient in order to recognize and facilitate the early termination of a developing exacerbation.

Further objects and advantages will become apparent from a consideration of the ensuing description and drawings

BRIEF SUMMARY OF THE INVENTION

The present invention provides a method for monitoring changes in the hemodynamic status of a heart failure patient by monitoring respiratory patterns. An implantable or other ambulatory monitor senses one or more of several physiologic signals to identify breathing patterns. The physiologic signals include transthoracic impedance, intracardiac electrograms and blood oxygen content. These physiologic signals are processed to generate physiologic parameter data that include the patient's respiratory rate, respiratory tidal volume, heart rate or arterial oxygen saturation. The physiologic parameter data are analyzed to derive an indication of periodic breathing. This is accomplished in a first preferred embodiment by a thresholding/binning technique to determine cycles of hyperpnic and hypopnic breathing within a periodic breathing episode. In a second preferred embodiment of the invention, this is accomplished by power spectral analysis of the physiologic parameter data.

The physiologic parameter data are derived from the physiologic signal that is sensed using a known physiologic sensor. In a preferred embodiment for the physiologic data of respiratory rate and tidal volume, transthoracic impedance is used providing a signal that changes with the lungs filling with air and expelling air.

Some physiologic parameter data such as respiratory rate, respiratory tidal volume, and heart rate are not continuous measures, but rather are defined at discrete intervals as suggested by the underlying process. For example, respiratory tidal volume and respiratory rate are both derived on a per-breath basis; thus, successive samples of these data would preferably be obtained at breath-to-breath intervals. As another example, heart rate is derived on a per-heartbeat basis; thus, successive samples of these data would preferably be obtained at heartbeat-to-heartbeat intervals. In contrast, other physiologic parameter data do not have an inherently preferred sampling interval. One such example is arterial oxygen saturation. For these cases, any convenient sampling interval could be adopted, for example at an interval related to heartbeat intervals or breath intervals. Determining the presence of periodic breathing provides an indicator of a current or impending exacerbation of a chronic heart failure condition. Appropriate steps such as initiation of pacing therapy to the heart or providing a warning to the patient or a healthcare provider of the condition may then be taken.

In one example of a preferred embodiment, respiratory tidal volume is monitored and a flag is set when the tidal volume exceeds or falls below predetermined thresholds indicative of hyperpnea or hypopnea and thus outside the normal breathing range. The time difference between repeated settings of this flag are tracked to determine if the difference is regular. Such a regular pattern is an indicator of periodic breathing which is itself an indicator of a CHF exacerbation. It is preferred that this monitoring occur during the time when the patient is at rest or asleep to avoid the introduction of extraneous influences such as may be present with patient exercise or other activity. Additionally, a long cycle length, on the order of about 15 seconds, or at least 3 breaths for excursions above or below the thresholds may be used as an added requirement to provide a clear indication of hyperpnea or hypopnea, respectively.

In an alternative embodiment of the invention, respiratory rate is monitored. The duration of excursions above a first threshold and below a second threshold are used as indicators of hyperpnea and hypopnea. As with the embodiment described above, these excursions provide an indicator of periodic breathing and a potential CHF exacerbation. Alternatively, power spectral analysis can be performed on respiratory rate or respiratory tidal volume data.

In another alternative embodiment of the invention, an electrogram signal is sensed from a sensing electrode. Heartbeat R-R intervals are calculated and a power spectrum analysis is performed on a sequence of such intervals. Changes in the very low frequency component of a power spectrum of R-R intervals are used to indicate the presence of periodic breathing. An analysis of heart rate excursions with the binning/thresholding method can also be used to indicate periodic breathing.

In yet another alternative embodiment of the invention, a blood oxygen saturation sensor is provided. Periodic changes in blood oxygen saturation are monitored as the indicator of periodic breathing. These data may be analyzed using either power spectral analysis or looking for excursions above and below predetermined thresholds.

BRIEF DESCRIPTION OF THE SEVERAL VIEWS OF THE DRAWINGS

These and various other features and aspects of the present invention will be readily understood with reference to the following detailed description taken in conjunction with the accompanying drawings, in which.

DETAILED DESCRIPTION OF THE INVENTION

Detection and monitoring of periodic breathing (PB), with and without periods of apnea (Cheyne-Stokes Respiration) is accomplished according to the invention by sensing a physiologic signal and deriving at least one of four independent physiologic measures or parameters from the physiologic signal. These data are then analyzed according to one of the embodiments of the invention. The physiologic measures are respiratory tidal volume, respiratory rate (B-B interval), arterial oxygen saturation ($SaO_2$) and heart rate (R-R interval). The data collected of these physiologic measures may then be analyzed by performing spectral analysis or thresholding/binning. Each analysis method can be applied to each measure or combination thereof. In the preferred embodiment, the physiologic measures are made when the patient has been identified as being at rest or asleep to prevent interference from activity-related respiratory variations.

Figure 1:
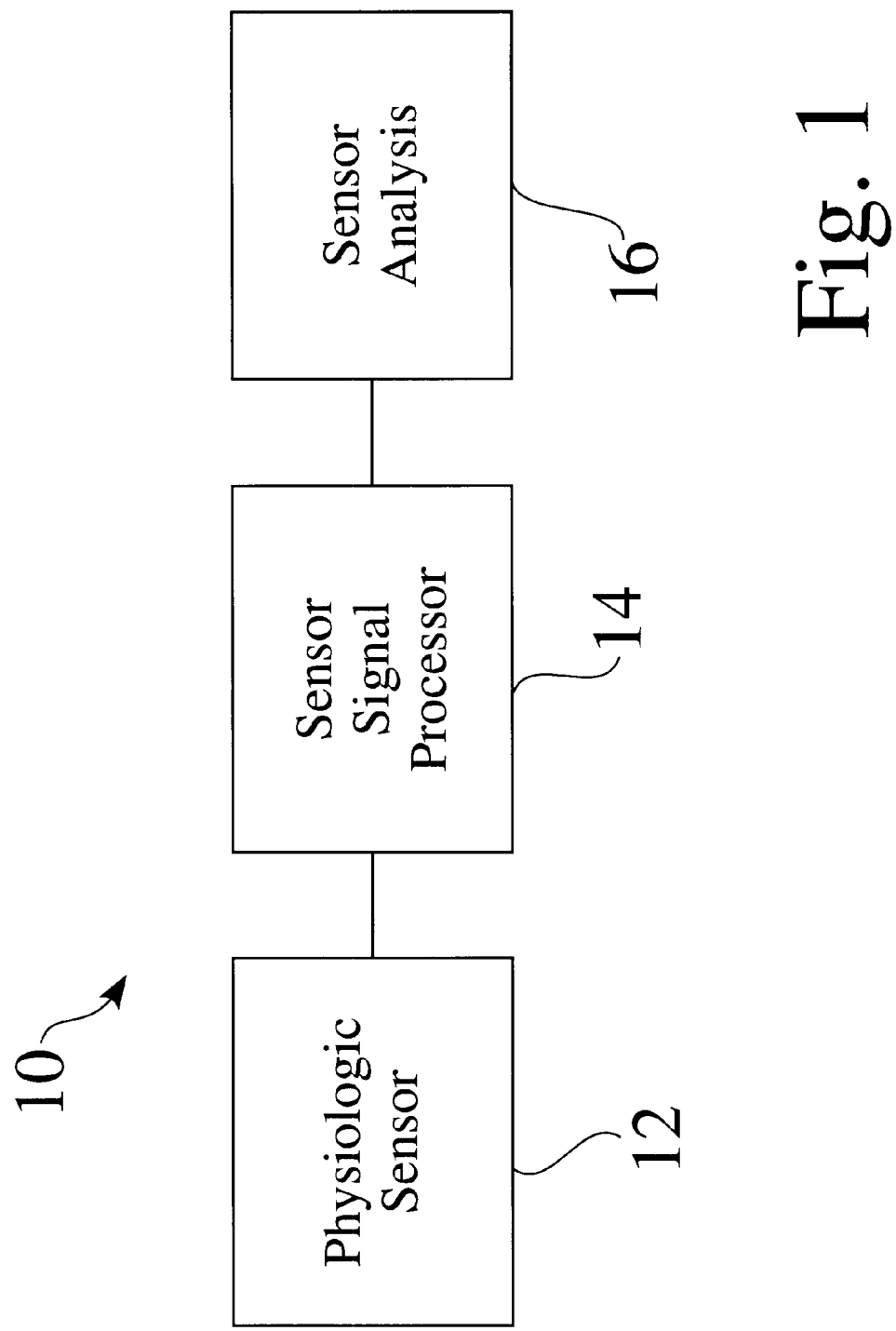
FIG. 1 shows a functional block diagram of a preferred embodiment of the invention.

The physiologic signals to be collected for deriving the physiologic measures may be collected using techniques well known to those skilled in the art. Referring to FIG. 1, a sensing or monitoring system 10 is provided. Such a system may be implemented in a pacemaker or implantable cardioverter defibrillator or may be part of a monitoring system that does not separately provide cardiac therapy. A physiologic sensor 12 is utilized to sense one or more physiologic signals. In a preferred embodiment, tidal volume and respiratory rate are determined from a sensed impedance plethysmography signal. Heart rate is determined from an electrocardiogram sensor placed in or around the heart or elsewhere in or on the chest. Oxygen saturation is measured using sensors known to those skilled in the art. The sensor signal is first processed in a signal processor 14 to extract data for analysis. Such analysis includes the measures mentioned hereinabove of tidal volume, respiratory rate, heart rate and arterial oxygen saturation. The physiologic data are then further analyzed in signal analysis processor 16. As will be understood by those skilled in the art, elements 14 and 16 may be implemented together or separately.

Figure 2:
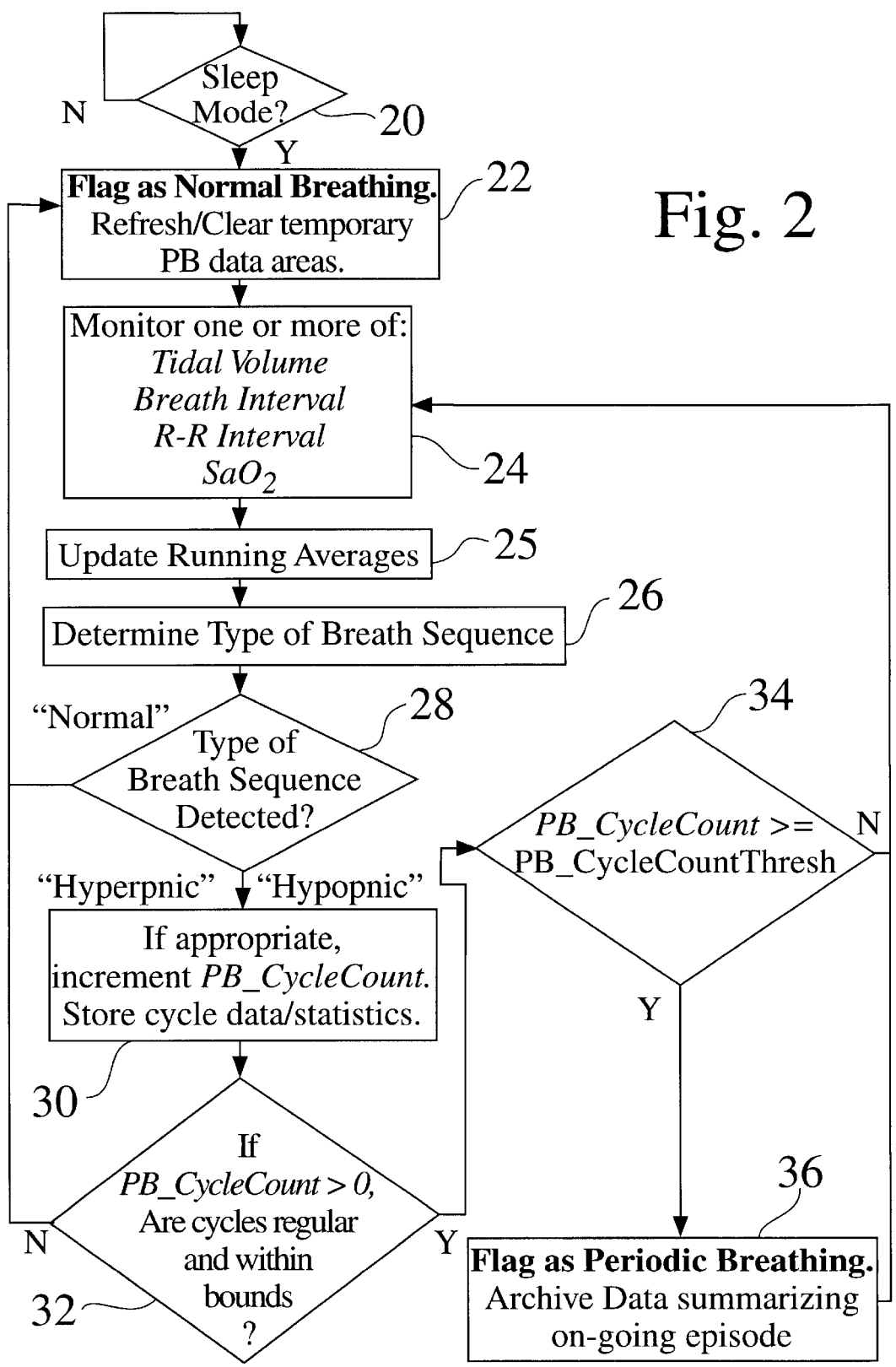
FIG. 2 shows a flow chart illustrating a preferred embodiment of the invention.

A first preferred embodiment of the invention will now be discussed with reference to FIG. 2. This method is a means of detecting cyclic behavior in any of the four physiologic parameters with simple comparisons of present value to programmed thresholds and subsequent binning. Inherent in this technique is comparison of a present value to a long-term average (LTA) for that measure. Long-term is defined here as being on the time scale of tens of minutes to hours. Thresholds are determined as percentages of the LTA. For illustrative purposes, further discussion will be based on tidal volume although the method can be equivalently implemented with the other three measures.

At step 20, a determination is made as to whether the patient is at rest or asleep. This can be done in various ways such as monitoring their position using an accelerometer to determine if they have been prone for an extended period or monitoring for a noted lack of activity for an extended period. If the patient is not at rest or asleep, the algorithm will not proceed until rest or sleep is detected. This avoids the introduction of extraneous influences such as may be present with patient exercise or other activity. At step 22, the system is reset and prior data are cleared from the bin memories. Next, at step 24, physiologic signals are acquired from the physiologic sensor. Depending on the implementation, the physiologic signals and derived physiologic parameter data may already be being acquired such as minute ventilation data used for rate responsive pacing or R-R intervals extracted from an electrogram for use by a pacemaker or defibrillator in arrhythmia detection. Running averages of the physiologic measure(s) are updated at step 25.

The data are analyzed to determine the type of breath sequence at step 26. If a normal breath sequence is detected, the algorithm is returned at step 28 to step 22. Otherwise, the appropriate bin for the periodic breathing cycle count for hyperpnic or hypopnic breathing is incremented at step 30. At step 32, determination is made of whether the cycles are within bounds, as will be discussed further below. If it is not, the method returns to step 22 to reset and begin again.

If the periodic breathing cycle count is within bounds, the count is compared to a preset threshold at step 34. A cycle is defined as a period over which the detected physiologic parameter crosses a threshold to enter a hyperpnic or hypopnic zone, exits the zone and crosses the threshold to reenter the zone. If the cycle count is less than the cycle count threshold, the algorithm returns to step 24 to collect more data from the physiologic sensor. If the cycle count equals or exceeds the cycle count threshold, the episode is flagged as Periodic Breathing at step 36 and the archived data on such episode are updated. The system returns to step 24 to continue to monitor the physiologic sensor(s) for indications of periodic breathing.

A determination of periodic breathing requires a minimum number of consecutive cycles, nominally at least 3, where each cycle length is within expected bounds (nominally 25–100 seconds). An insufficient number of cycles or cycle lengths out of bounds will cause the bins to be reset.

A specific method for determining of the type of breath sequence detected will now be discussed. Episodes of hyperpnea are defined as 100+XX% of the LTA, nominally XX=50, so 150% of LTA. Episodes of hypopnea are defined as 100−YY% of LTA, nominally YY=50, so 50% of the LTA. In the device of the invention, these parameters are programmable over a fairly broad range and are optimized based on clinical experience. Determination of hyperpnic and hypopnic events can be made on a breath-by-breath basis or as a function of time. For example, in one embodiment of the invention the algorithm requires a sustained excursion above the hyperpnic threshold for at least N consecutive breaths (nominally 3) or for at least M seconds (nominally 15 sec.) or for x-of-y breaths (nominally 3-of-4). The preferred implementation is x-of-y breaths as the requirement of N consecutive breaths can also be implemented in the x-of-y approach by setting both x and y to the same value.

A determination of classic periodic breathing requires hyperpnic and hypopnic events in succession without an extended intervening period of normal breathing. Extended normal breathing (defined as greater than Z successive breaths or a period of time or x-of-y criteria) resets the bins that have been incremented for hyperpnic and hypopnic events.

It is noted that determination of other modes of periodic breathing, not before described in the classic literature but yet potentially of interest, will also be detected. This includes cycles between only hyperpnea and normal or cycles between only hypopnea and normal. Extended normal breathing in these modes would also cause the resetting of bins.

Figure 3:
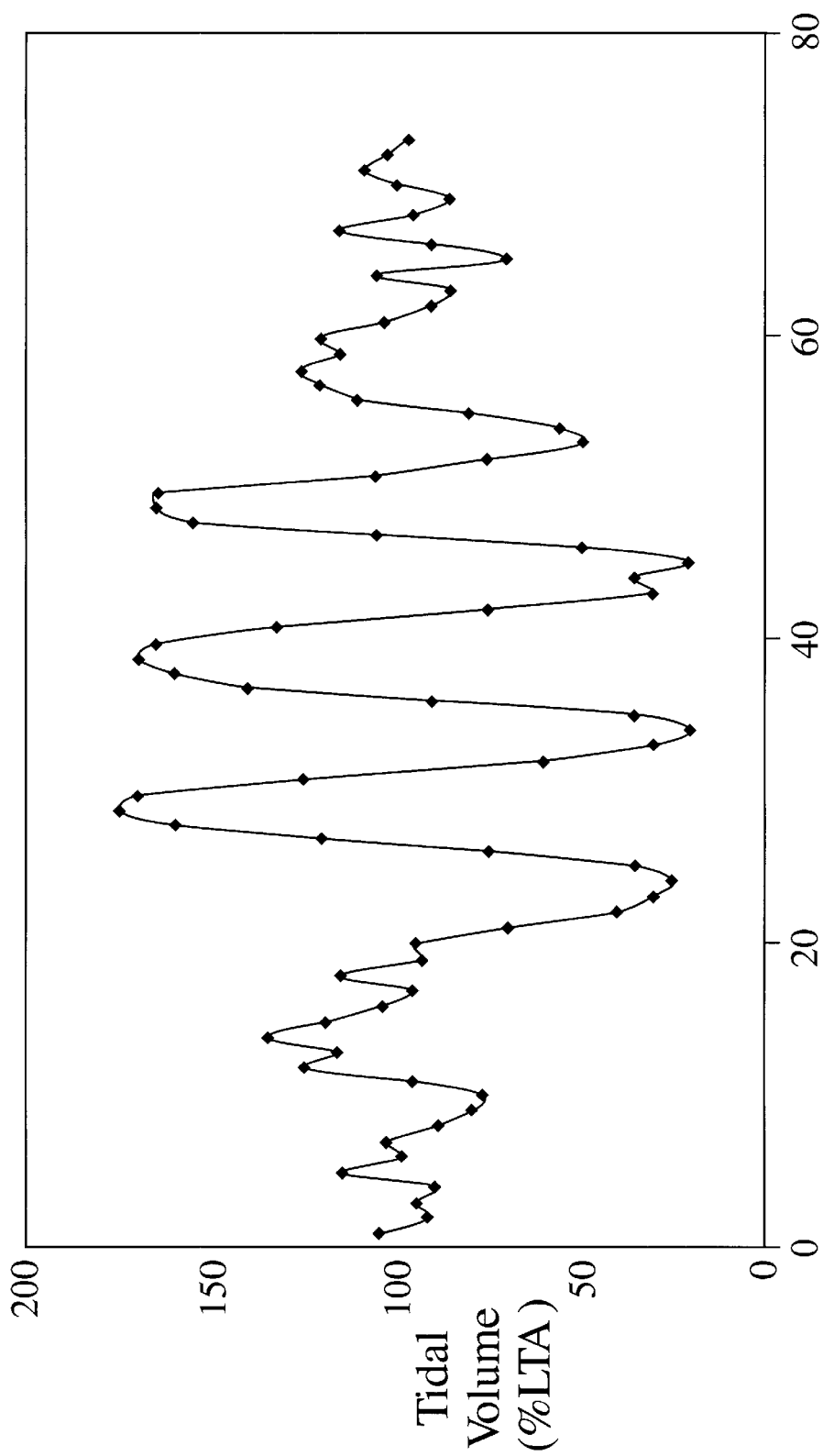
FIG. 3 shows an exemplary representation of periodic breathing based on tidal volume measure alternating between hypopnic and hyperpnic breathing.
Figure 4:
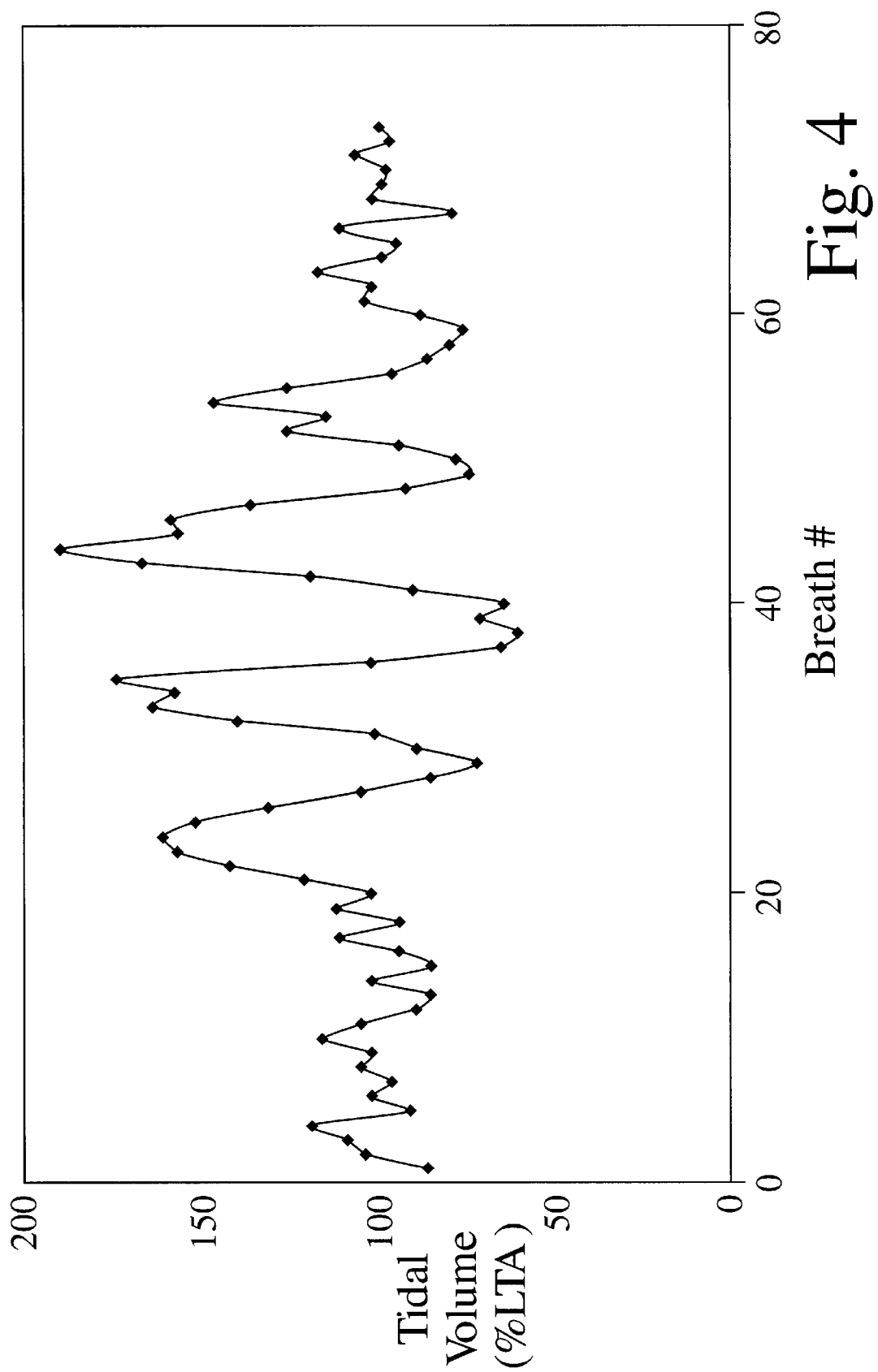
FIG. 4 shows an exemplary representation of periodic breathing based on tidal volume measure alternating between hyperpnic and normal breathing.

Referring now to FIGS. 3 and 4, exemplary representations of periodic breathing are shown. In FIG. 3, the tidal volume measure alternates between hypopnic and hyperpnic breathing where the measured tidal volume falls below 50% of the Long Term Average for at least 3 breaths and exceeds 150% of the LTA for at least 3 breaths, respectively. In FIG. 4, the periodic breathing alternates between hyperpnic breathing and normal breathing.

Achievement of true periodic breathing criteria will initiate archiving of the sequence. The data to be archived for a periodic breathing sequence include any or all of the following: time/breaths of hyperpnea per cycle, time/breaths of hypopnea per cycle, time of apnea per cycle (if any), largest hyperpnic excursion per cycle, largest hypopnic excursion per cycle, number of cycles the sequence was sustained and average cycle length of periodic breathing in the sequence. Note that apnea is defined as a special form of hypopnea where the tidal volume has not only decreased but breathing has actually ceased, to begin again several seconds later.

In an alternative preferred embodiment, spectral analysis is performed on the measured physiologic parameter. All four physiologic measures show cyclic variation during periodic or Cheyne-Stokes breathing with a median frequency of 0.02 Hz, ranging from about 0.01 to about 0.04 Hz. To identify whether a signal (any of the four measures) has a significant frequency component in that range, power spectral analysis can be performed using any traditional, well-known technique.

Archived data will be retrieved later by physician interrogation of the device and used to evaluate disease progression/regression and effectiveness of therapy. Alternatively, the data may be downloaded by automatic telemetry for transmission to a healthcare provider. Additionally, the periodic breathing data may be an indicator of increased mortality risk, for example from ventricular arrhythmias. The clinician may take appropriate steps to respond to such indications.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A method for monitoring changes of the disease state of a heart failure patient comprising the steps of:
   (a) sensing a physiologic signal that varies in response to changes in breathing patterns to provide physiologic parameter data indicative of periodic breathing;
   (b) analyzing said physiologic parameter data by determining whether said physiologic parameter data exceeds a first threshold or falls below a second threshold for a predetermined number of breaths to derive an indication of periodic breathing; and
   (c) providing an indication of a change of disease state of said heart failure patient.

2. A method for monitoring changes of the disease state of a heart failure patient comprising the steps of:
   (a) determining that the patient is at rest or asleep;
   (b) sensing the patient's physiologic signal;
   (c) deriving a physiological parameter from said physiologic signal for successive intervals;
   (d) performing a power spectral analysis on the sequence of successive physiologic parameter measures;
   (e) determining the magnitude of a very low frequency component of said power spectrum in the range of about 0.01 to about 0.04 Hz; and
   (f) analyzing said very low frequency component of said power spectrum to determine if said patient is experiencing periodic breathing and to provide an indication of changes of the disease state of said patient.

3. The method of claim 2 wherein said intervals are breath-to-breath intervals.

4. The method of claim 2 wherein said intervals are heartbeat-to-heartbeat intervals.

5. A method for monitoring changes of the disease state of a heart failure patient comprising the steps of:
   (a) sensing a physiologic signal that varies in response to changes in breathing patterns to provide physiologic parameter data indicative of periodic breathing;
   (b) analyzing said physiologic parameter data by determining whether said physiologic parameter data exceeds a first threshold or falls below a second threshold for a predetermined number of heart beats to derive an indication of periodic breathing; and
   (c) providing an indication of a change of disease state of said heart failure patient.

6. A method for monitoring changes of the disease state of a heart failure patient comprising the steps of:
  (a) sensing a physiologic signal that varies in response to changes in breathing patterns to provide physiologic parameter data indicative of periodic breathing;
  (b) analyzing said physiologic parameter data by determining whether said physiologic parameter data exceeds a first threshold or falls below a second threshold for x of y data points where y is a positive integer greater than or equal to 2 and x is a positive integer less than or equal to y to derive an indication of periodic breathing; and
  (c) providing an indication of a change of disease state of said heart failure patient.

7. A method for monitoring changes of the disease state of a heart failure patient comprising the steps of:
  (a) determining that said patient is at rest or asleep;
  (b) sensing a physiologic signal that varies in response to changes in breathing patterns to provide physiologic parameter data indicative of periodic breathing;
  (c) analyzing said physiologic parameter data to derive an indication of periodic breathing; and
  (d) providing an indication of a change of disease state of said heart failure patient.

8. A method for monitoring changes of the disease state of a heart failure patient comprising the steps of:
  (a) sensing a physiologic signal that varies in response to changes in breathing patterns to provide physiologic parameter data indicative of periodic breathing;
  (b) defining a hyperpnic zone for physiologic data falling above a first threshold and a hypopnic zone for physiologic data falling below a second threshold and a normal zone between said hyperpnic and hypopnic zones;
  (c) identifying successive occurrences when said physiologic data falls in one of said hyperpnic or hypopnic zones for a predetermined duration;
  (d) analyzing said physiologic parameter data to determine if a periodic breathing pattern exists based on the sequence of occurrences when said data falls in each of said zones; and
  (e) providing an indication of a change of disease state of said heart failure patient.

9. The method of claim 8 wherein said duration is measured in breaths.

10. The method of claim 8 wherein said duration is measured in heartbeats.

11. The method of claim 8 wherein said duration is measured in time.

12. The method of claim 8 wherein said duration is satisfied for x of y data points where y is a positive integer greater than or equal to 2 and x is a positive integer less than or equal to y.

13. A method for monitoring changes of the disease state of a heart failure patient comprising the steps of:
  (a) sensing a physiologic signal from said patient;
  (b) deriving a physiologic parameter from said physiologic signal for successive intervals;
  (c) determining when said physiologic parameter exceeds a first predetermined threshold for a predetermined duration as an indicator of hyperpnea;
  (d) determining when said physiologic parameter is below a second predetermined threshold for a predetermined duration as an indicator of hypopnea;
  (e) repeating steps (a) through (d) to identify a sequence of occurrences when said physiologic parameter is greater than said first threshold or less than said second threshold; and
  (f) analyzing said sequence of occurrences to determine if said patient is experiencing periodic breathing and to provide an indication of changes of the disease state of said patient.

14. The method of claim 13 wherein said intervals are breath-to-breath intervals.

15. The method of claim 13 wherein said intervals are heartbeat-to-heartbeat intervals.

16. The method of claim 13 wherein said step of deriving a physiologic parameter from said physiologic signal at said intervals includes deriving at least one of respiratory tidal volume, respiratory rate, heart rate and arterial oxygen saturation.

17. The method of claim 13 wherein a cycle comprises a sequence of occurrences when said physiologic parameter crosses from a hyperpnic or hypopnic condition to a different condition and back again and where said step (f) includes requiring at least three cycles to determine periodic breathing with each cycle lasting between about 25 seconds and 100 seconds.

18. The method of claim 13 wherein said predetermined duration is measured in breaths.

19. The method of claim 13 wherein said predetermined duration is measured in heart beats.

20. The method of claim 13 wherein said predetermined duration is measured in time.

21. The method of claim 13 wherein said predetermined duration is satisfied for x of y data points where y is a positive integer greater than or equal to 2 and x is a positive integer less than or equal to y.

22. The method of claim 13 and further including the step of determining that said patient is at rest or asleep prior to commencing steps (a) through (f).

* * * * *